United States Patent
Cong et al.

(10) Patent No.: US 10,646,537 B2
(45) Date of Patent: May 12, 2020

(54) TRADITIONAL CHINESE MEDICINE FOR TREATING ABDOMINAL OBESITY

(71) Applicant: INFINITUS (CHINA) COMPANY LTD., Jiang Men, Guangdong (CN)

(72) Inventors: Renhuai Cong, Guangdong (CN); Fangli Ma, Guangdong (CN); Chung Wah Ma, Guangdong (CN); Xiaoling Wang, Guangdong (CN); Lingyun Xiao, Guangdong (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 69 days.

(21) Appl. No.: 15/792,493

(22) Filed: Oct. 24, 2017

(65) Prior Publication Data

US 2018/0264068 A1    Sep. 20, 2018

(30) Foreign Application Priority Data

Mar. 15, 2017    (CN) .......................... 2017 1 0154227

(51) Int. Cl.
| | |
|---|---|
| *A61K 36/8994* | (2006.01) |
| *A61K 36/484* | (2006.01) |
| *A61K 36/752* | (2006.01) |
| *A61K 36/185* | (2006.01) |

(52) U.S. Cl.
CPC ........ *A61K 36/8994* (2013.01); *A61K 36/185* (2013.01); *A61K 36/484* (2013.01); *A61K 36/752* (2013.01)

(58) Field of Classification Search
None
See application file for complete search history.

(56) References Cited

U.S. PATENT DOCUMENTS

2015/0296851 A1* 10/2015 Zhao .................. A23F 3/34
426/2

FOREIGN PATENT DOCUMENTS

| CN | 1135908 A | * | 11/1996 |
| CN | 104171204 A | * | 12/2014 |

OTHER PUBLICATIONS

Zhao, Y. et al. Chemical Compositions, Chromatographic Fingerprints and Antioxidant Activities of Citri *Exocarpium rubrum* (Juhong). Chinese Medicine 12(6)1-15, 2017. (Year: 2017).*

* cited by examiner

*Primary Examiner* — Ralph J Gitomer
(74) *Attorney, Agent, or Firm* — Yue (Robert) Xu; Apex Attorneys at Law, LLP

(57) ABSTRACT

The present disclosure relates to the field of health food technology, in particular to a traditional Chinese medicine composition, preparation method and use thereof. The traditional Chinese medicine composition is made from Coicis Semen, Hippophae Fructus, Citri Rubrum Exocarpium and Glycyrrhizae Radix et Rhizoma. The traditional Chinese medicine composition uses less species of Chinese herbs and has significant effect on reducing the circumference of waist and abdomen, reducing the weight of visceral fat and anti-inflammation by reasonable combination, and does not have side effects.

2 Claims, No Drawings

TRADITIONAL CHINESE MEDICINE FOR TREATING ABDOMINAL OBESITY

CROSS-REFERENCE TO RELATED APPLICATIONS

The present application claims a priority to Chinese patent application No. 201710154227.5, as filed on Mar. 15, 2017 and titled with "TRADITIONAL CHINESE MEDICINE COMPOSITION, PREPARATION METHOD AND USE THEREOF", and the disclosure of which is incorporated herein by reference.

FIELD

The present disclosure relates to the field of health food technology, in particular to a traditional Chinese medicine composition, preparation method and use thereof.

BACKGROUND

Abdominal obesity mainly refers to fat deposition in the abdominal cavity, manifesting an increase in the circumference of waist and abdomen. There are many factors that affect the increase in the circumference of waist and abdomen, such as unhealthy eating habits, lack of physical activity, being sedentary due to occupational habits, etc. The risk of developing complications in people with abdominal obesity is much greater than that in people with systemic obesity. Moreover, intra-abdominal fat is very different from subcutaneous fat. It is more harmful than subcutaneous fat, and it releases more harmful factors than subcutaneous fat does. Abdominal obesity is likely to damage internal organs, makes people more likely to suffer from high blood pressure, diabetes, hyperlipidemia, cholelithiasis, hyperuricemia and other diseases, so the detriment is severer.

Abdominal obesity is the main type of obesity among Chinese people. The follow-up observation of 2778 subjects by the Medical College of Soochow University also found that at the same time that some of the individuals' BMIs decrease, their waist circumferences may not significantly decrease, or even may increase; while at the same time that the BMIs rise, the waist circumference may reduce. Therefore, determining whether a person is obese by his or her weigh only is a misconception. It is likely to classify people with normal BMI but high waist into low-risk groups, but in fact, disease risk in this part of people is still high. Therefore, controlling the abdominal obesity is of great significance.

So far, people mainly use exercise and drugs to lose weight. Mostly, once the exercise stops, it is likely to gain the weight back. Losing weight by drugs is mainly through suppressing central appetite developing anorexia and satiety, reducing nutrient absorption, increasing energy consumption, etc., it usually has certain side effects, such as diarrhea and arrhythmia, even liver damage, kidney damage, etc. Therefore, people look forward to developing the traditional Chinese medicine products which have simple components, less toxic and side effects. However, for the treatment of abdominal obesity, traditional Chinese medicine products have been rarely reported.

Patent Publication No. CN103070924A discloses a traditional Chinese medicine composition for treating metabolic syndrome, its preparation method and application. Said traditional Chinese medicine composition is prepared by the following Chinese herbs: Rids Cornutae Folium 6-30 weight parts, Nelumbinis Folium 6-30 weight parts, Mori Folium 6-30 weight parts. The traditional Chinese medicine composition with pharmaceutically acceptable carrier can be used to produce the pharmaceutical preparations for treating metabolic syndrome, in particular to produce the pharmaceutical preparations for treating abdominal obesity, type-II diabetes, hyperlipidemia or atherosclerotic disease. There is still a need for a new type of traditional Chinese medicine composition for effective treatment of abdominal obesity.

SUMMARY

In view of the above, the present disclosure provides a traditional Chinese medicine composition, preparation method and use thereof. The traditional Chinese medicine composition can reduce the circumference of waist and abdomen, reduce the weight of visceral fat, effectively improve the concentrations of inflammation-related factors IL-10, IL-18, PAI-1, adiponectin, TNF-$\alpha$, IL6, CRP, etc. in serum. It may be used to prevent or treat abdominal obesity, and its effect is significantly better than the effect of each single herb in the composition.

In order to achieve the object of the present disclosure, the following technical solution(s) is provided by the present disclosure.

The present disclosure provides a traditional Chinese medicine composition, which is made from Coicis Semen, Hippophae Fructus, Citri Rubrum Exocarpium and Glycyrrhizae Radix et Rhizoma.

It was recorded in ancient books of traditional Chinese medicine that "fat man" was due to the overfeeding greasy and surfeit flavor, lack of excise, resulted in "Spleen Obstruction", which caused "Liver Stagnation", that means, spleen failed in transportation, the transportation of the water and food essence was blocked, and transportation and transformation of water-dampness weekened. As time passed, it would lead to Qi obstruction, triple energizers disharmony, water-dampness retention and phlegm turbidity accumulation, resulted in the formation of obesity.

Coicis Semen, sweet and bland, cool, in the spleen, stomach and lung meridian, can fortify the spleen, drain dampness, clear heat, expel pus, remove impediment and relax sinews. It is used to treat spleen deficiency, diarrhea, pain in muscle, joint pain, edema, athlete's foot, white vaginal discharge, etc.

Hippophae Fructus, sour, astringent, mild, has functions in suppressing cough, resolving phlegm, invigorating the stomach, promoting digestion, activating blood and dissipating stasis. It is mainly used to treat cough and excessive phlegm, lung abscess, indigestion, food accumulation, abdominal pain, stomach pain, enteritis, amenorrhea, traumatic bruise and swelling.

Citri Rubrum Exocarpium, acrid, bitter, mild, in the lung and spleen meridian, can dissipate cold, dry dampness, promote circulation of Qi, resolve phlegm, smooth the middle, and dissipate binds. It is used to treat wind-cold type cough, itchy throat, excessive phlegm, food accumulation, liquor damage, nausea and vomiting, chest distress.

Glycyrrhizae Radix et Rhizoma, sweet, neutral, non-toxic, in spleen, stomach and lung meridian. It invigorates spleen-stomach and replenishes Qi, relaxes tension, relieves pain, moistens the lung, suppresses cough, purges fire, detoxifies, harmonizes the functions and properties of herbs. It is used to treat spleen-stomach weakness, tire and lack of strength, palpitation and shortness of breath, cough, excessive phlegm, stomach, abdomen, and limb spasm and pain, carbuncle, sore-toxin, and relieves drug toxic and drastic actions.

The combination of the traditional Chinese medicines mentioned above enhance the functions in fortifying the spleen, nourishing the stomach, inducing diuresis, alleviating edema, drying dampness and resolving phlegm. It was proved by tests of the present disclosure that they can reduce the circumference of waist and abdomen, reduce the weight of visceral fat, and effectively improve the concentrations of inflammation-related factors IL-10, IL-18, PAI-1, adiponectin, TNF-α, IL6, CRP, etc. in serum. It may be used to prevent or treat abdominal obesity, and its effect is significantly better than the effect of each single herb.

Preferably, by weight, the dosage of each raw material is:

| Coicis Semen | 10-100 parts; |
|---|---|
| Hippophae Fructus | 5-50 parts; |
| Citri Rubrum Exocarpium | 5-50 parts; and |
| Glycyrrhizae Radix et Rhizoma | 2-30 parts. |

Preferably, by weight, the dosage of each raw material is:

| Coicis Semen | 20-100 parts; |
|---|---|
| Hippophae Fructus | 5-50 parts; |
| Citri Rubrum Exocarpium | 5-50 parts; and |
| Glycyrrhizae Radix et Rhizoma | 2-30 parts. |

More preferably, by weight, the dosage of each raw material is:

| Coicis Semen | 50 parts; |
|---|---|
| Hippophae Fructus | 25 parts; |
| Citri Rubrum Exocarpium | 25 parts; and |
| Glycyrrhizae Radix et Rhizoma | 12.5 parts. |

In one embodiment provided by the present disclosure, by weight, the dosage of each raw material is:

| Coicis Semen | 20 parts; |
|---|---|
| Hippophae Fructus | 35 parts; |
| Citri Rubrum Exocarpium | 10 parts; and |
| Glycyrrhizae Radix et Rhizoma | 20 parts. |

In another embodiment provided by the present disclosure, by weight, the dosage of each raw material is:

| Coicis Semen | 70 parts; |
|---|---|
| Hippophae Fructus | 10 parts; |
| Citri Rubrum Exocarpium | 35 parts; and |
| Glycyrrhizae Radix et Rhizoma | 5 parts. |

In another embodiment provided by the present disclosure, by weight, the dosage of each raw material is:

| Coicis Semen | 100 parts; |
|---|---|
| Hippophae Fructus | 10 parts; |
| Citri Rubrum Exocarpium | 10 parts; and |
| Glycyrrhizae Radix et Rhizoma | 15 parts. |

The present disclosure also provides a use(s) of the traditional Chinese medicine composition(s) in the preparation of medicaments and health foods for treating abdominal obesity.

In the embodiments provided by the present disclosure, treating abdominal obesity refers to one or more of reducing the circumference of waist and belly, decreasing Lee's index, reducing the weight of visceral fat, or improving effectively the concentrations of inflammation-related factor: IL-10, IL-18, PAI-1, adiponectin, TNF-α, IL6 and CRP in serum.

The present disclosure also provides methods for preparing the traditional Chinese medicine composition, which comprises: mixing Coicis Semen, Hippophae Fructus, Citri Rubrum Exocarpium and Glycyrrhizae Radix et Rhizoma, adding water, soaking, decocting, filtering, and obtaining the traditional Chinese medicine composition.

Preferably, the quantity of water is 3-10 times as much as the total weight of raw materials; soaking time is 0.25 h-2 h; number of times to decoct is 1-5 times; time of each decoction is 1 h-4 h.

In the embodiments provided by the present disclosure, the quantity of water is 8 times as much as the total weight of raw materials; soaking time is 1 h; numbers of times to decoct is 2 times; time of each decoction is 2 h.

Preferably, a concentration step is also included after the filtration.

In the embodiments provided by the present disclosure, the concentration is: concentrating until soluble solids concentration is 80%.

The present disclosure also provides a type of pharmaceutical, which comprises the traditional Chinese medicine composition provided by the present disclosure.

Preferably, the pharmaceutical also comprises pharmaceutically acceptable excipient(s).

Preferably, the dosage forms of the pharmaceutical(s) are paste, granule, pill, powder, tablet, capsule, oral agent or syrup. However, the dosage form of the pharmaceutical(s) is not limited thereto, any dosage form considered by those of ordinary skill in the art as a feasible one is within the scope of the present disclosure.

The present disclosure also provides a health food, which comprises the traditional Chinese medicine composition(s) provided in the present disclosure.

Preferably, the health foods further comprise a food-acceptable food additive(s).

Preferably, the dosage forms of the health foods are granule, capsule, syrup, tablet, powder, gummy candy, emulsion or oral solution. However, the dosage form of the health foods is not limited thereto, any dosage form considered by those of ordinary skill in the art as a feasible one is within the scope of the present disclosure.

The present disclosure provides a traditional Chinese medicine composition, preparation method and use thereof. The traditional Chinese medicine composition is made from Coicis Semen, Hippophae Fructus, Citri Rubrum Exocarpium and Glycyrrhizae Radix et Rhizoma. The technical effects of the present disclosure are:

The traditional Chinese medicine composition of the present disclosure is made from raw material(s) that includes Coicis Semen, Hippophae Fructus, Citri Rubrum Exocarpium and Glycyrrhizae Radix et Rhizoma. The traditional Chinese medicine composition(s) uses less specie(s) of Chinese herbs and has significant effects on reducing the circumference of waist and abdomen, reducing the weight of visceral fat and anti-inflammation by reasonable combination, and does not have side effects. The results of tests showed that the traditional Chinese medicine composition(s) of the present disclosure can reduce the circumference of waist and abdomen, reduce the weight of visceral fat, and effectively improve the concentrations of IL-10, IL-18, PAI-1, adiponectin, TNF-α, IL6, CRP and other inflammation-related factors in serum. It may be used to prevent or treat abdominal obesity, and its effect is significantly better than the effect of each single herb.

DETAILED DESCRIPTION OF EMBODIMENTS

The present disclosure discloses a traditional Chinese medicine composition, preparation method and use thereof, and it can be achieved by one of ordinary skill in the art through improving process parameters based on the contents here. In particular, it needs to be pointed out that all similar substitutions and modifications are apparent to those of ordinary skill in the art and are considered to be included in the present disclosure. The method and use of the present disclosure have been described by way of preferred embodiments, and it will be apparent to those of ordinary skill in the art that changes and combinations of the method and use described herein may be made without departing from the content, spirit and scope of the present invention to achieve and use the techniques of the present disclosure.

The raw materials and the excipients used in the traditional Chinese medicine composition, the preparation method and use thereof provided by the present disclosure are all commercially available.

The present disclosure is further described in conjunction with the following Examples:

Example 1

Preparation of the Traditional Chinese Medicine Composition
1. Raw Materials
The weight proportion of every raw materials: Coicis Semen 50 parts, Hippophae Fructus 25 parts, Citri Rubrum Exocarpium 25 parts, Glycyrrhizae Radix et Rhizoma 12.5 parts.
2. Preparation Method
The active pharmaceutical ingredients of Coicis Semen, Hippophae Fructus, Citri Rubrum Exocarpium and Glycyrrhizae Radix et Rhizoma were mixed, soaked in added water, and the amount of water added was 8 times as much as the weight of raw materials, and the soaking time was 1 h. Decoction was performed twice, 2 h each time. The decoction solution was filtered and concentrated until soluble solids concentration was 80%, said traditional Chinese medicine composition of the present disclosure was obtained.

Example 2

Preparation of the Traditional Chinese Medicine Composition
1. Raw Materials
The weight proportion of every raw materials: Coicis Semen 20 parts, Hippophae Fructus 35 parts, Citri Rubrum Exocarpium 10 parts, Glycyrrhizae Radix et Rhizoma 20 parts.
2. Preparation Method
The preparation method was the same as that in Example 1.

Example 3

Preparation of the Traditional Chinese Medicine Composition
1. Raw Materials
The weight proportion of every raw materials: Coicis Semen 70 parts, Hippophae Fructus 10 parts, Citri Rubrum Exocarpium 35 parts, Glycyrrhizae Radix et Rhizoma 5 parts.
2. Preparation Method
The preparation method was the same as that in Example 1.

Example 4

Preparation of the Traditional Chinese Medicine Composition
1. Raw Materials
The weight proportion of every raw materials: Coicis Semen 100 parts, Hippophae Fructus 10 parts, Citri Rubrum Exocarpium 10 parts, Glycyrrhizae Radix et Rhizoma 15 parts.
2. Preparation Method
The preparation method was the same as that in Example 1.

Example 5

Pharmacodynamic Experiment of the Traditional Chinese Medicine Compositions for Treating Abdominal Obesity
1. Experimental Materials
(1) Main Reagents
Feed (whole milk protein, corn starch, sucrose, soybean oil), minerals, vitamins, raw materials were self-purchased, were completed by the preparation method of Hubei University of Traditional Chinese Medicine, were completed by the processing of the Experimental Animal Center of Hubei University of Traditional Chinese Medicine.

Chlorpromazine injection, Southwest Pharmaceutical Co., Ltd., national medicine permission number H50020116.

Kit, Nanjing Jiancheng Bioengineering Institute.
(2) Experimental Animals
SD rats, male, SPF grade, body weight (180±15) g, provided by the Animal Experimental Center of Hubei University of Traditional Chinese Medicine.
(3) Main Instruments
Electronic analytical balance, BS124S, Startorius (Germany); microplate reader, Bio-Rad Laboratories, Inc. (USA); ultra low-temperature freezer, Thermo Fisher Scientific Inc. (USA); ultra pure water machine, Mill-Q II, Milipore (Bedford, Mass., USA); DDL-5 freezing centrifuge, Shanghai Anting Scientific Instrument Factory.
2. Test Methods
Healthy male SD rats were housed in normal maintenance feed (equivalent to normal diet) for 3 days.

Blank group, model group, test group were set up respectively. The blank control group was given intraperitoneal injection of saline once and freely drank and ate; the model group and each test group were all injected intraperitoneally with chlorpromazine 3 mg/kg once and freely drank and ate. During the experiments, the blank group was given basic feed; the model group and the test groups were given medium-fat feed (including: 140 g/kg whole milk protein, corn starch 538.1 g/kg, sucrose 87.6 g/kg, soybean oil 137 g/kg), and minerals and vitamins (minerals 35 g/kg, vitamin 50 g/kg, choline 2.3 g/kg) were complemented into it. All of them continued 15 days.

After the model group was set up, each test group took the test sample for 6 weeks: the low, medium and high dosage groups of Example 1 (4.5:9.0:18.0 g/kg), high dosage group (18.0 g/kg) of Examples 2, 3 and 4, the administration volume was 2.0 mL/kg. The model group was given the corresponding dosage of distilled water.

3. Test Indexes

After 6 weeks, the animals were sacrificed, blood was taken and dissection was performed. The circumference of waist and abdomen, body weight and body length of the rats were measured accurately and the Lee's index was calculated.

Perinephric fat, epididymal fat, epicardial fat, retroperitoneal fat, greater omental fat and mesenteric fat, and total visceral adipose tissue (VAT) were weighed.

The concentrations of inflammation-related factors in serum: IL-10, IL-18, PAI-1 (Plasminogen Activator Inhibitor), adiponectin, IL-6, CRP were determined.

4. Statistical Methods

In general, the analysis of variance was used; however, it was needed that the homogeneity of variance test was firstly performed according to the variance analysis procedure. If the variance was homogeneous, the F value was calculated. $F<F_{0.05}$, conclusion: the difference between the averages of each group was not significant. $F \geq F_{0.05}$, $p \leq 0.05$, statistical analysis was performed by the pairwise comparison between the average of multiple experimental groups and the average of control group. For non-normal or non-homogeneous data, appropriate transformation(s) of variables was carried out. The transformed data was subjected to statistical analysis after meeting the normal or homogeneous variance requirements. If the transformed data still did not reach the normal or homogeneous variance after the transformation of variables, statistical analysis was performed by rank sum test.

5. Results of the Experiment

After the completion of the experiments, the index level changes of each group were shown in Table 1 to Table 3.

TABLE 1

The effects of each dosage group on Lee's index and circumference of waist and abdomen of rats

| Group | Number of cases | Lee's index | Circumference of waist and abdomen |
|---|---|---|---|
| Blank group | 15 | 293.61 ± 1.08 | 14.25 ± 0.05 |
| Model group | 15 | 309.18 ± 1.22[#] | 17.90 ± 0.10[#] |
| Low dosage group of Example 1 | 15 | 301.51 ± 2.25[X] | 17.01 ± 0.15 |
| Medium dosage group of Example 1 | 15 | 300.59 ± 4.70[X] | 16.23 ± 0.05[X] |
| High dosage group of Example 1 | 15 | 295.08 ± 0.19[X] | 15.05 ± 0.05[X] |
| High dosage group of Example 2 | 15 | 295.12 ± 0.22[X] | 15.22 ± 0.24[X] |
| High dosage group of Example 3 | 15 | 296.33 ± 1.13[X] | 15.99 ± 0.15[X] |
| High dosage group of Example 4 | 15 | 295.98 ± 2.34[X] | 15.45 ± 0.08[X] |

Note:
[#]compared with the blank group, p < 0.05;
[X]compared with the model group, p < 0.05.

The comparisons of Lee's index of each rat group are shown in Table 1. The difference was statistical comparing the Lee's index of the rats in the model group with that in the blank group (p<0.05). There was statistical difference between the Lee's index in each sample group and the model group (p<0.05). As to the index of circumference of waist and abdomen, there was statistical difference comparing each sample group with the model group (p<0.05).

TABLE 2

The comparisons of body fat (g) of each rat group

| Group | Retroperitoneal fat | Epididymal fat | Epicardial fat | Greater omental fat | Perinephric fat | Mesenteric fat | Visceral adipose tissue (VAT) |
|---|---|---|---|---|---|---|---|
| Blank group | 2.33 ± 0.60 | 1.58 ± 0.29 | 0.31 ± 0.09 | 0.98 ± 0.09 | 0.35 ± 0.05 | 2.56 ± 0.20 | 8.11 ± 0.32 |
| Model group | 3.98 ± 0.65[#] | 1.95 ± 0.38[#] | 0.39 ± 0.23[#] | 1.39 ± 0.31[#] | 0.42 ± 0.14 | 4.10 ± 1.10[#] | 13.39 ± 2.61[#] |
| Low dosage group of Example 1 | 3.79 ± 1.82 | 1.86 ± 0.45 | 0.38 ± 0.20 | 1.39 ± 0.43 | 0.38 ± 0.10 | 2.76 ± 1.08[X] | 11.48 ± 5.24 |
| Medium dosage group of Example 1 | 3.10 ± 0.41[X] | 1.57 ± 0.68[X] | 0.36 ± 0.17 | 1.36 ± 0.10 | 0.35 ± 0.22 | 2.70 ± 0.49[X] | 10.15 ± 2.19[X] |
| High dosage group of Example 1 | 3.02 ± 0.40[X] | 1.50 ± 0.39[X] | 0.34 ± 0.01[X] | 1.35 ± 0.21[X] | 0.28 ± 0.17[X] | 2.67 ± 0.23[X] | 9.89 ± 1.26[X] |
| High dosage group of Example 2 | 3.17 ± 0.25[X] | 1.49 ± 0.27[X] | 0.35 ± 0.08[X] | 1.35 ± 0.34[X] | 0.29 ± 0.16[X] | 2.69 ± 0.56[X] | 9.99 ± 1.11[X] |
| High dosage group of Example 3 | 3.15 ± 0.23[X] | 1.51 ± 0.44[X] | 0.34 ± 0.10[X] | 1.35 ± 0.27[X] | 0.30 ± 0.18[X] | 2.71 ± 0.44[X] | 10.01 ± 1.67[X] |
| High dosage group of Example 4 | 3.13 ± 0.41[X] | 1.50 ± 0.23[X] | 0.35 ± 0.11[X] | 1.36 ± 0.16[X] | 0.31 ± 0.27[X] | 2.78 ± 0.47[X] | 10.09 ± 1.26[X] |

Note:
[#]compared with the blank group, p < 0.05;
[X]compared with the model group, p < 0.05.

There were statistical differences comparing the weight of retroperitoneal fat, epididymal fat, epicardial fat, greater omental fat, mesenteric fat and total visceral adipose tissue (VAT) of the rats in the model group with those in the blank group (p<0.05), which indicated the success of modeling.

As to the indexes of weight of retroperitoneal fat, epididymal fat, mesenteric fat and total visceral adipose tissue, there were statistical differences between the medium dosage group of Example 1 and the model group (p<0.05).

As to the indexes of weight of retroperitoneal fat, epicardial fat, greater omental fat, perinephric fat, epididymal fat, mesenteric fat and total visceral adipose tissue (VAT), there were statistical differences between high dosage groups of Examples 1 to 4 and the model group were statistically significant(p<0.05).

TABLE 3

The comparisons of inflammation-related factors of each group

| Group | IL-10 (pg/mL) | IL-18 (pg/mL) | PAI-1 (ng/mL) | Adiponectin (ng/mL) | CRP (ng/mL) | IL-6 (pg/mL) |
|---|---|---|---|---|---|---|
| Blank group | 85.93 ± 16.98 | 34.92 ± 3.98 | 16.83 ± 0.26 | 19.535 ± 10.524 | 1.256 ± 0.262 | 96.068 ± 9.869 |
| Model group | 26.33 ± 6.924# | 133.40 ± 25.96# | 40.67 ± 5.22# | 4.55 ± 0.276# | 5.381 ± 0.253# | 239.757 ± 17.210# |
| Low dosage group of Example 1 | 35.58 ± 3.87✕ | 70.32 ± 6.10✕ | 28.82 ± 0.99✕ | 6.710 ± 0.392✕ | 4.679 ± 0.217 | 196.557 ± 7.996✕ |
| Medium dosage group of Example 1 | 41.52 ± 16.31✕ | 66.88 ± 18.24✕ | 26.95 ± 2.84✕ | 9.226 ± 1.823✕ | 4.091 ± 0.218✕ | 202.266 ± 11.841✕ |
| High dosage group of Example 1 | 56.12 ± 2.303✕ | 59.42 ± 1.721✕ | 25.67 ± 1.96✕ | 13.053 ± 1.504✕ | 3.485 ± 0.748✕ | 186.876 ± 13.656✕ |
| High dosage group of Example 2 | 50.12 ± 11.13✕ | 56.77 ± 1.234✕ | 25.11 ± 1.11✕ | 7.234 ± 1.112✕ | 3.662 ± 0.225✕ | 196.876 ± 3.332✕ |
| High dosage group of Example 3 | 52.12 ± 10.09✕ | 59.23 ± 0.728✕ | 26.67 ± 0.96✕ | 7.123 ± 0.347✕ | 3.485 ± 0.447✕ | 191.363 ± 8.225✕ |
| High dosage group of Example 4 | 49.12 ± 12.43✕ | 59.67 ± 9.721✕ | 26.23 ± 0.88✕ | 6.934 ± 0.593✕ | 3.485 ± 0.388✕ | 190.245 ± 17.656✕ |

Note:
compared with the blank group, $p < 0.05$;
✕compared with the model group, $p < 0.05$.

Comparing the concentrations of IL-10, IL-18, PAI-1, adiponectin, IL-6 and CRP of the rats in the model group with those in the blank group, all the differences were statistically meaningful ($p<0.05$), which indicated the success of modeling.

There were statistic differences between the concentrations of IL-10, IL-18, PAI-1, adiponectin, IL-6 and CRP of each sample group ($p<0.05$).

6. Summary of the Experiment

Comprehensive analysis of the above data shows that all of the sample groups can reduce the circumference of waist and abdomen, and eliminate the visceral fat to varying degrees. There are significant differences when comparing with the model group.

Compared with the blank group, all of the inflammation-related factors IL-10, IL-18, PAI-1, adiponectin, TNF-α, IL6, CRP, etc. in serum of model group show significant increase or decrease, while each sample group can improve the change(s) of these factors to certain degrees. It indicates that each test group has an intervention effect on the imbalance of inflammation-related factors in abdominal obesity model.

Example 6

Pharmacodynamic Experiment of the Traditional Chinese Medicine Compositions for Treating Abdominal Obesity 1. Experimental Materials (1) Main Reagents Feed (whole milk protein, corn starch, sucrose, soybean oil), minerals, vitamins, raw materials were self-purchased, were completed by the preparation method of Hubei University of Traditional Chinese Medicine, were completed by the processing of the Experimental Animal Center of Hubei University of Traditional Chinese Medicine.

Chlorpromazine injection, Southwest Pharmaceutical Co., Ltd., national medicine permission number H50020116.

Kit, Nanjing Jiancheng Bioengineering Institute.

(2) Animals

SD rats, male, SPF grade, body weight (180±15)g, provided by the Animal Experimental Center of Hubei University of Traditional Chinese Medicine.

(3) Main Instruments

Electronic analytical balance, BS124S, Startorius (Germany); microplate reader, Bio-Rad Laboratories, Inc. (USA); ultra low-temperature freezer, Thermo Fisher Scientific Inc. (USA); ultra pure water machine, Mill-Q II, Milipore (Bedford, Mass., USA); DDL-5 freezing centrifuge, Shanghai Anting Scientific Instrument Factory.

2. Test Methods

Healthy male SD rats were housed in normal maintenance feed (equivalent to normal diet) for 3 days.

Blank group, model group, test group were set up respectively. The blank control group was given intraperitoneal injection of saline once and freely drank and ate; the model group and each test group were injected intraperitoneally with chlorpromazine 3 mg/kg once and freely drank and ate. During the experiment, the blank group was given basic feed; the model group and the test groups were given medium-fat feed (including: 140 g/kg whole milk protein, corn starch 538.1 g/kg, sucrose 87.6 g/kg, soybean oil 137 g/kg), and minerals and vitamins (minerals 35 g/kg, vitamin 50 g/kg, choline 2.3 g/kg) were complemented into it. All of them continued 15 days.

After the model was set up, each test group took the test sample for 6 weeks: the high dosage group of Example 1 (18.0 g/kg), single herb group of Coicis Semen, Hippophae Fructus, Citri Rubrum Exocarpium and Glycyrrhizae Radix et Rhizoma (18.0 g/kg, preparation method of the single herb was the same as in Example 1), the administration volume was 2.0 mL/kg. The model group was given the corresponding dosage of distilled water.

3. Test Indexes

After 6 weeks, the animals were sacrificed, blood was taken and dissection was performed. The circumference of waist and abdomen, body weight and body length of rats were measured accurately and Lee's index was calculated.

Perinephric fat, epididymal fat, epicardial fat, retroperitoneal fat, greater omental fat and mesenteric fat, and total visceral adipose tissue (VAT) were weighed.

The concentrations of inflammation-related factors in serum: IL-10, IL-18, PAI-1 (Plasminogen Activator Inhibitor), adiponectin, IL-6, CRP were determined.

4. Statistical Methods

In general, the analysis of variance was used, however, it was needed that homogeneity of variance test was firstly performed according to the variance analysis procedure. If the variance was homogeneous, the F value was calculated. $F<F_{0.05}$, conclusion: the difference between the averages of each group was not significant. $F \geq F_{0.05}$, $p \leq 0.05$, statistical analysis was performed by the pairwise comparison between the average of multiple experimental groups and the average of control group. For non-normal or non-homogeneous data, appropriate transformation(s) of variables was carried out. The transformed data was subjected to statistical analysis after meeting the normal or homogeneous variance requirements. If the transformed data still did not reach the normal or homogeneous variance after the transformation of variables, statistical analysis was performed by rank sum test.

5. Results of the Experiment

After the completion of the experiments, the index level changes of each group are shown in Table 4 to Table 6.

TABLE 4

The effects of each dosage group on Lee's index and circumference of waist and abdomen of rats

| Group | Number of cases | Lee's index | Circumference of waist and abdomen (cm) |
|---|---|---|---|
| Blank group | 15 | 293.61 ± 1.08 | 14.25 ± 0.05 |
| Model group | 15 | 309.18 ± 1.22# | 17.90 ± 0.10# |
| Coicis Semen group | 15 | 301.45 ± 1.25✕* | 17.01 ± 0.15* |
| Hippophae Fructus group | 15 | 302.51 ± 0.93✕* | 16.98 ± 0.06* |
| Citri Rubrum Exocarpium group | 15 | 303.51 ± 1.09✕* | 16.87 ± 0.11* |
| Glycyrrhizae Radix et Rhizoma group | 15 | 299.51 ± 0.23✕* | 17.11 ± 0.23* |
| High dosage group of Example 1 | 15 | 295.08 ± 0.19✕ | 15.05 ± 0.05✕ |

Note:
compared with the blank group, p < 0.05;
✕compared with the model group, p < 0.05;
*stands for being compared with the high dosage group of Example 1, p < 0.05.

The comparisons of Lee's index of each rat group are shown in Table 4. The difference between the Lee's index of rats in the model group and the blank group was statistically meaningful (p<0.05). There was statistical difference between the Lee's index in each sample group and the model group (p<0.05). As to the circumference of waist and abdomen, there was no statistical difference between each single herb group and the model group.

Also, there were statistical differences between the Lee's indexes in the high dosage group and each single herb group (p<0.05). As to the circumference of waist and abdomen, there were significant differences between Example 1 group and each single herb group (p<0.05).

TABLE 5

The comparisons of body fat (g) of each rat group

| Group | Retroperitoneal fat | Epididymal fat | Epicardial fat | Greater omental fat | Perinephric fat | Mesenteric fat | Visceral adipose tissue (VAT) |
|---|---|---|---|---|---|---|---|
| Blank group | 2.33 ± 0.60 | 1.58 ± 0.29 | 0.31 ± 0.09 | 0.98 ± 0.09 | 0.35 ± 0.05 | 2.56 ± 0.20 | 8.11 ± 0.32 |
| Model group | 3.98 ± 0.65# | 1.95 ± 0.38# | 0.39 ± 0.23# | 1.39 ± 0.31# | 0.42 ± 0.14 | 4.10 ± 1.10# | 13.39 ± 2.61# |
| Coicis Semen group | 3.81 ± 0.86* | 1.70 ± 0.33* | 0.38 ± 0.09* | 1.39 ± 0.03* | 0.39 ± 0.03* | 2.87 ± 1.08✕* | 11.95 ± 0.46* |
| Hippophae Fructus group | 3.83 ± 0.93* | 1.78 ± 0.63* | 0.37 ± 0.12* | 1.38 ± 0.21* | 0.38 ± 0.11* | 2.98 ± 0.35✕ | 10.98 ± 0.06* |
| Citri Rubrum Exocarpium group | 3.60 ± 1.73* | 1.81 ± 0.09* | 0.38 ± 0.23* | 1.38 ± 0.44* | 0.40 ± 0.03* | 2.70 ± 1.27✕ | 10.09 ± 0.15* |
| Glycyrrhizae Radix et Rhizoma group | 3.66 ± 1.74* | 1.80 ± 0.12* | 0.37 ± 0.21* | 1.38 ± 0.09* | 0.38 ± 0.09* | 2.74 ± 0.06✕* | 10.54 ± 0.45* |
| High dosage group of Example 1 | 3.02 ± 0.40✕ | 1.50 ± 0.39✕ | 0.34 ± 0.01✕ | 1.35 ± 0.21✕ | 0.28 ± 0.17✕ | 2.67 ± 0.23✕ | 9.89 ± 1.26✕ |

Note:
compared with the blank group, p < 0.05;
✕compared with the model group, p < 0.05;
*stands for being compared with the high dosage group of Example 1, p < 0.05.

As to the indexes of weight of retroperitoneal fat, epididymal fat, epicardial fat, greater omental fat, mesenteric fat and total visceral adipose tissue (VAT), there was statistical difference between each single herb group and the high dosage group of Example 1 of the sample groups (p<0.05).

TABLE 6

The comparisons of inflammation-related factors of each group

| Group | IL-10 (pg/mL) | IL-18 (pg/mL) | PAI-1 (ng/mL) | Adiponectin (ng/mL) | CRP (ng/mL) | IL-6 (pg/mL) |
|---|---|---|---|---|---|---|
| Blank group | 85.93 ± 16.98 | 34.92 ± 3.98 | 16.83 ± 0.26 | 19.535 ± 10.524 | 1.256 ± 0.262 | 96.068 ± 9.869 |
| Model group | 26.33 ± 6.924# | 133.40 ± 25.96# | 40.67 ± 5.22# | 4.55 ± 0.276# | 5.381 ± 0.253# | 239.757 ± 17.210# |
| Coicis Semen group | 34.67 ± 9.37✕* | 78.32 ± 7.76✕* | 30.82 ± 0.03✕* | 6.053 ± 1.275✕* | 4.669 ± 0.210* | 200.334 ± 11.345✕* |
| Hippophae Fructus group | 35.78 ± 3.09✕* | 89.67 ± 6.18✕* | 36.82 ± 0.77✕* | 6.539 ± 1.206✕* | 4.876 ± 0.287* | 190.043 ± 21.333✕* |

TABLE 6-continued

The comparisons of inflammation-related factors of each group

| Group | IL-10 (pg/mL) | IL-18 (pg/mL) | PAI-1 (ng/mL) | Adiponectin (ng/mL) | CRP (ng/mL) | IL-6 (pg/mL) |
|---|---|---|---|---|---|---|
| Citri Rubrum Exocarpium group | 30.34 ± 5.56$^{X*}$ | 70.53 ± 8.10$^{X*}$ | 28.82 ± 0.34$^{X*}$ | 5.883 ± 1.407$^{X*}$ | 4.544 ± 0.654* | 209.986 ± 8.235$^{X*}$ |
| Glycyrrhizae Radix et Rhizoma group | 30.11 ± 5.39$^{X*}$ | 95.11 ± 11.66$^{X*}$ | 32.82 ± 0.89$^{X*}$ | 5.932 ± 1.512$^{X*}$ | 4.987 ± 0.198* | 203.045 ± 7.978$^{X*}$ |
| High dosage group of Example 1 | 56.12 ± 2.303$^{X}$ | 59.42 ± 1.721$^{X}$ | 25.67 ± 1.96$^{X}$ | 13.053 ± 1.504$^{XX}$ | 3.485 ± 0.748$^{X}$ | 186.876 ± 13.656$^{X*}$ |

Note:
compared with the blank group, $p < 0.05$;
Xcompared with the model group, $p < 0.05$;
*stands for being compared with the high dosage group of Example 1, $p < 0.05$.

The differences between the concentrations of IL-10, IL-18, PAI-1, adiponectin, IL-6 and CRP in the high dosage group of Example 1 and each single herb group were statistically meaningful ($p<0.05$).

6. Summary of the Experiment

Comprehensive analysis of the above data shows that all sample groups can reduce the circumference of waist and abdomen, and eliminate the visceral fat to varying degrees. There are significant differences when comparing the sample group with each single herb group.

The inflammation-related factors IL-10, IL-18, PAI-1, adiponectin, TNF-α, IL6, CRP, etc. all show significant increases or decreases in serum in the embodiments, the improvement function of sample group is better than that of each single herb group. These results indicate that the traditional Chinese medicine composition(s) of the present disclosure has an intervention effect on the imbalance of inflammation-related factors in abdominal obesity model.

Comparative Example 1

The experimental method was referred to that in Example 6, pharmacodynamics of multiple combinations of each traditional Chinese medicine extracts were investigated. Results are shown in Table 7 to Table 9.

TABLE 7

The effects of each dosage group on Lee's index and circumference of waist and abdomen of rats

| No. | Group | Number of cases | Lee's index | Circumference of waist and abdomen (cm) |
|---|---|---|---|---|
| 1 | Blank group | 15 | 293.61 ± 1.08 | 14.25 ± 0.05 |
| 2 | Model group | 15 | 309.18 ± 1.22# | 17.90 ± 0.10# |
| 3 | High dosage group of Example 1 | 15 | 295.08 ± 0.19 | 15.05 ± 0.05 |
| 4 | Coicis Semen 50 parts + Hippophae Fructus 25 parts | 15 | 300.13 ± 0.12$^{Δ}$ | 16.87 ± 0.17$^{Δ}$ |
| 5 | Coicis Semen 50 parts + Citri Rubrum Exocarpium 25 parts | 15 | 298.11 ± 0.22$^{Δ}$ | 16.78 ± 0.28$^{Δ}$ |
| 6 | Coicis Semen 50 parts + Glycyrrhizae Radix et Rhizome 12.5 parts | 15 | 298.62 ± 0.20$^{Δ}$ | 17.03 ± 0.18$^{Δ}$ |
| 7 | Hippophae Fructus 25 parts + Citri Rubrum Exocarpium 25 parts | 15 | 299.98 ± 0.19$^{Δ}$ | 16.56 ± 0.17$^{Δ}$ |
| 8 | Hippophae Fructus 25 parts + Glycyrrhizae Radix et Rhizome 12.5 parts | 15 | 301.51 ± 0.08$^{Δ}$ | 16.34 ± 0.23$^{Δ}$ |
| 9 | Citri Rubrum Exocarpium 25 parts + Glycyrrhizae Radix et Rhizoma 12.5 parts | 15 | 299.90 ± 0.10$^{Δ}$ | 16.69 ± 0.25$^{Δ}$ |
| 10 | Coicis Semen 50 parts + Hippophae Fructus 25 parts + Citri Rubrum Exocarpium 25 parts | 15 | 298.89 ± 0.17$^{Δ}$ | 16.51 ± 0.07$^{Δ}$ |
| 11 | Coicis Semen 50 parts + Hippophae Fructus 25 parts | 15 | 297.38 ± 0.14$^{Δ}$ | 16.48 ± 0.11$^{Δ}$ |
| 12 | Hippophae Fructus 25 parts + Citri Rubrum Exocarpium 25 parts | 15 | 299.51 ± 0.08$^{Δ}$ | 16.60 ± 0.15$^{Δ}$ |
| 13 | Coicis Semen 50 parts + Citri Rubrum Exocarpium 25 parts | 15 | 299.98 ± 0.06$^{Δ}$ | 16.71 ± 0.10$^{Δ}$ |

Note:
Δcompared with the high dosage group of Example 1, $p < 0.05$.

TABLE 8

The comparisons of body fat (g) of each rat group

| No. | Retroperitoneal fat | Epididymal fat | Epicardial fat | Great omental fat | Perinephric fat | Mesenteric fat | Visceral adipose tissue (VAT) |
|---|---|---|---|---|---|---|---|
| 1 | 2.33 ± 0.60 | 1.58 ± 0.29 | 0.31 ± 0.09 | 0.98 ± 0.09 | 0.35 ± 0.05 | 2.56 ± 0.20 | 8.11 ± 0.32 |
| 2 | 3.98 ± 0.65# | 1.95 ± 0.38# | 0.39 ± 0.23# | 1.39 ± 0.31# | 0.42 ± 0.14 | 4.10 ± 1.10# | 13.39 ± 2.61# |
| 3 | 3.02 ± 0.40 | 1.50 ± 0.39 | 0.34 ± 0.01$^\Delta$ | 1.35 ± 0.21 | 0.28 ± 0.17 | 2.67 ± 0.23 | 9.89 ± 1.26 |
| 4 | 3.60 ± 0.73$^\Delta$ | 1.81 ± 0.09$^\Delta$ | 0.38 ± 0.23$^\Delta$ | 1.38 ± 0.04$^\Delta$ | 0.40 ± 0.03$^\Delta$ | 2.70 ± 1.27 | 11.09 ± 0.15$^\Delta$ |
| 5 | 3.62 ± 0.82$^\Delta$ | 1.81 ± 0.35$^\Delta$ | 0.38 ± 0.20$^\Delta$ | 1.39 ± 0.03$^\Delta$ | 0.38 ± 0.10$^\Delta$ | 2.71 ± 0.08$^\Delta$ | 11.16 ± 2.24$^\Delta$ |
| 6 | 3.70 ± 0.65$^\Delta$ | 1.81 ± 0.04$^\Delta$ | 0.38 ± 0.09$^\Delta$ | 1.38 ± 0.04$^\Delta$ | 0.40 ± 0.01$^\Delta$ | 2.70 ± 0.27 | 11.02 ± 0.35$^\Delta$ |
| 7 | 3.60 ± 0.98$^\Delta$ | 1.82 ± 0.13$^\Delta$ | 0.37 ± 0.04$^\Delta$ | 1.39 ± 0.11$^\Delta$ | 0.39 ± 0.02$^\Delta$ | 2.69 ± 1.26 | 11.19 ± 0.07$^\Delta$ |
| 8 | 3.61 ± 0.73$^\Delta$ | 1.82 ± 0.12$^\Delta$ | 0.36 ± 0.23$^\Delta$ | 1.38 ± 0.27$^\Delta$ | 0.39 ± 0.01$^\Delta$ | 2.69 ± 0.78 | 10.99 ± 0.10$^\Delta$ |
| 9 | 3.60 ± 0.56$^\Delta$ | 1.83 ± 0.14$^\Delta$ | 0.38 ± 0.13$^\Delta$ | 1.39 ± 0.17$^\Delta$ | 0.38 ± 0.09$^\Delta$ | 2.68 ± 0.35 | 10.82 ± 0.16$^\Delta$ |
| 10 | 3.65 ± 0.92$^\Delta$ | 1.84 ± 0.09$^\Delta$ | 0.37 ± 0.14$^\Delta$ | 1.38 ± 0.15$^\Delta$ | 0.38 ± 0.03$^\Delta$ | 2.67 ± 1.34 | 10.54 ± 0.21$^\Delta$ |
| 11 | 3.72 ± 0.03$^\Delta$ | 1.85 ± 0.13$^\Delta$ | 0.38 ± 0.13$^\Delta$ | 1.39 ± 0.14$^\Delta$ | 0.37 ± 0.13$^\Delta$ | 2.68 ± 0.46 | 10.52 ± 0.20$^\Delta$ |
| 12 | 3.73 ± 0.11$^\Delta$ | 1.86 ± 0.02$^\Delta$ | 0.37 ± 0.11$^\Delta$ | 1.39 ± 0.23$^\Delta$ | 0.37 ± 0.07$^\Delta$ | 2.68 ± 0.24 | 10.23 ± 0.11$^\Delta$ |
| 13 | 3.79 ± 0.22$^\Delta$ | 1.86 ± 0.01$^\Delta$ | 0.38 ± 0.15$^\Delta$ | 1.39 ± 0.12$^\Delta$ | 0.37 ± 0.06$^\Delta$ | 2.68 ± 0.27$^\Delta$ | 10.32 ± 0.05$^\Delta$ |

Note:
the sample groups to which the numbers in Table 8 correspond are the same as that in Table 7;
$^\Delta$stands for being compared with the high dosage group of Example 1, $p < 0.05$.

TABLE 9

The comparisons of inflammation-related factors of each group

| No. | IL-10 (pg/mL) | IL-18 (pg/mL) | PAI-1 (ng/mL) | Adiponectin (ng/mL) | CRP (ng/mL) | IL-6 (pg/mL) |
|---|---|---|---|---|---|---|
| 1 | 85.93 ± 16.98 | 34.92 ± 3.98 | 16.83 ± 0.26 | 19.535 ± 10.524 | 1.256 ± 0.262 | 96.068 ± 9.869 |
| 2 | 26.33 ± 6.924# | 133.40 ± 25.96# | 40.67 ± 5.22# | 4.550 ± 0.276# | 5.381 ± 0.253# | 239.757 ± 17.210# |
| 3 | 56.12 ± 2.303 | 59.42 ± 1.721 | 25.67 ± 1.96 | 13.053 ± 1.504 | 3.485 ± 0.748 | 186.876 ± 13.656 |
| 4 | 30.34 ± 5.45$^\Delta$ | 70.27 ± 5.10$^\Delta$ | 28.78 ± 0.23$^\Delta$ | 6.542 ± 0.392$^\Delta$ | 4.544 ± 0.654$^\Delta$ | 209.986 ± 6.0467$^\Delta$ |
| 5 | 30.58 ± 3.73$^\Delta$ | 70.11 ± 6.23$^\Delta$ | 30.06 ± 0.09$^\Delta$ | 6.499 ± 0.235$^\Delta$ | 4.679 ± 0.217$^\Delta$ | 196.534 ± 7.274$^\Delta$ |
| 6 | 31.23 ± 2.11$^\Delta$ | 72.11 ± 7.41$^\Delta$ | 29.02 ± 0.33$^\Delta$ | 6.607 ± 0.346$^\Delta$ | 4.566 ± 0.213$^\Delta$ | 207.275 ± 6.235$^\Delta$ |
| 7 | 32.56 ± 3.04$^\Delta$ | 71.53 ± 3.89$^\Delta$ | 28.67 ± 0.45$^\Delta$ | 6.609 ± 0.305$^\Delta$ | 4.600 ± 0.217$^\Delta$ | 209.268 ± 5.235$^\Delta$ |
| 8 | 32.32 ± 4.34$^\Delta$ | 70.53 ± 4.37$^\Delta$ | 27.99 ± 0.25$^\Delta$ | 6.579 ± 0.284$^\Delta$ | 4.557 ± 0.109$^\Delta$ | 200.234 ± 3.246$^\Delta$ |
| 9 | 33.25 ± 4.67$^\Delta$ | 69.53 ± 4.10$^\Delta$ | 28.92 ± 0.35$^\Delta$ | 6.610 ± 0.107$^\Delta$ | 4.563 ± 0.213$^\Delta$ | 197.9344 ± 4.257$^\Delta$ |
| 10 | 32.76 ± 1.90$^\Delta$ | 71.53 ± 3.45$^\Delta$ | 27.93 ± 0.46$^\Delta$ | 6.703 ± 0.238$^\Delta$ | 4.587 ± 0.123$^\Delta$ | 195.123 ± 1.235$^\Delta$ |
| 11 | 33.04 ± 5.33$^\Delta$ | 70.53 ± 5.12$^\Delta$ | 26.90 ± 0.67$^\Delta$ | 6.701 ± 0.123$^\Delta$ | 4.623 ± 0.100$^\Delta$ | 199.100 ± 1.126$^\Delta$ |
| 12 | 32.34 ± 0.56$^\Delta$ | 70.53 ± 2.24$^\Delta$ | 28.32 ± 0.34$^\Delta$ | 6.597 ± 0.146$^\Delta$ | 4.245 ± 0.253$^\Delta$ | 200.345 ± 4.245$^\Delta$ |
| 13 | 30.98 ± 5.23$^\Delta$ | 69.53 ± 4.16$^\Delta$ | 28.52 ± 0.23 | 6.631 ± 0.174$^\Delta$ | 4.535 ± 0.166$^\Delta$ | 204.245 ± 8.345$^\Delta$ |

Note:
the sample groups to which the numbers in Table 9 correspond are the same as that in Table 7;
$^\Delta$stands for being compared with the high dosage group of Example 1, $p < 0.05$.

Results Analysis

Comprehensive analysis of the above data shows that all indexes in each different combination of single herb are significantly different compared with the high dosage group of Example 1. These results indicate that the formula combination of Example 1 has significant effects on reducing the circumference of waist and abdomen, reducing the visceral fat and anti-inflammation. The foregoing is only a preferred embodiment(s) of the present disclosure.

It should be pointed out that a number of improvements and modifications may also be made by those of ordinary skill in the art without departing from the principles of the present disclosure, and these improvements and modifications are also considered to be within the scope of the present disclosure.

The invention claimed is:

1. A traditional Chinese medicine composition for treating abdominal obesity, which is made from the following raw materials consisting of:

| | |
|---|---|
| *Coicis Semen* | 50 parts; |
| *Hippophae Fructus* | 25 parts; |
| *Citri Rubrum Exocarpium* | 25 parts; and |
| *Glycyrrhizae Radix et Rhizoma* | 12.5 parts. |

2. A health food, comprising the traditional Chinese medicine composition according to claim 1.

* * * * *